United States Patent [19]

Letchworth et al.

[11] 4,419,350

[45] Dec. 6, 1983

[54] CARBOFURAN COMPOSITIONS FOR PROBLEM SOILS

[75] Inventors: Peter E. Letchworth, Cupertino; Thomas B. Williamson, Santa Clara, both of Calif.

[73] Assignee: Stauffer Chemical Company, Westport, Conn.

[21] Appl. No.: 318,295

[22] Filed: Nov. 5, 1981

[51] Int. Cl.³ .................. A01N 43/08; A01N 57/00
[52] U.S. Cl. .................................... 424/225; 424/285
[58] Field of Search ............................. 424/225, 285

[56] References Cited

U.S. PATENT DOCUMENTS

| | | | |
|---|---|---|---|
| 2,770,567 | 11/1956 | Wedemeyer et al. | 167/22 |
| 3,193,452 | 7/1965 | Jäger et al. | 424/225 |
| 3,474,170 | 10/1969 | Scharpf | 424/285 |
| 3,474,171 | 10/1969 | Scharpf | 424/285 |
| 4,004,001 | 1/1977 | Large et al. | 424/225 |
| 4,006,229 | 2/1977 | Drabek | 424/225 |
| 4,035,490 | 7/1977 | Pitt | 424/225 |
| 4,257,987 | 3/1981 | Arend et al. | 424/203 |
| 4,292,068 | 9/1981 | Van Hoogstraten et al. | 71/88 |
| 4,302,466 | 11/1981 | Heywang et al. | 424/285 |

OTHER PUBLICATIONS

McEwan et al., Journal of Economic Entomology, vol. 58, No. 2, pp. 369–370.
Armbrust et al., Journal of Economic Entomology, vol. 58, No. 5, pp. 940–942.

*Primary Examiner*—Allen J. Robinson
*Attorney, Agent, or Firm*—Paul R. Martin

[57] ABSTRACT

The insecticide carbofuran (2,3-dihydro-2,2-dimethyl-7-benzofuranyl methylcarbamate) is combined with an organophosphorus additive of the formula

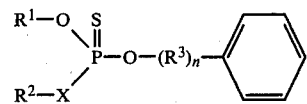

in which
$R^1$ is $C_1$–$C_4$ alkyl,
$R^2$ is $C_1$–$C_4$ alkyl,
$R^3$ is $C_1$–$C_4$ alkylene,
X is oxygen or sulfur, and
n is zero or one, for application to soil where previous applications of carbofuran have resulted in successive decreases in the insecticidal activity of carbofuran. The lost activity of the carbofuran is thereby restored.

10 Claims, No Drawings

CARBOFURAN COMPOSITIONS FOR PROBLEM SOILS

BACKGROUND OF THE INVENTION

1. Field of the Invention

This invention relates to the insecticide carbofuran and to its use in soils where its insecticidal activity declines upon repeated applications. In particular, this invention relates to means of restoring the insecticidal activity of carbofuran in such soils.

2. Description of the Prior Art

"Carbofuran" is the common name for 2,3-dihydro-2,2-dimethyl-7-benzofuranyl methylcarbamate, which is represented by the following formula

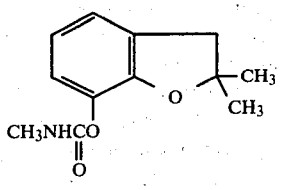

This compound is claimed in U.S. Pat. Nos. 3,474,170 and 3,474,171, both issued on Oct. 21, 1969, to W. G. Scharpf, and both assigned to FMC Corporation. In addition to its common name, the compound is known to the public under the FMC Corporation trademark "Furadan ®" and the Bayer AG trademark "Curaterr ®". In its technical form, the compound is a colorless crystalline solid. It is normally used, however, as a wettable powder containing 750 g active ingredient per kilogram, a flowable paste containing 480 g active ingredient per liter, or granules containing 20, 30, 50, or 100 g active ingredient per kilogram.

Carbofuran is a systemic insecticide, acaricide, and nematicide. It is applied to plant foliage at 0.25 to 1.0 kilograms active ingredient per hectare (kg/ha) for the control of insects and mites, broadcast at 6 to 10 kg/ha for the control of nematodes, or applied to soil (particularly seed furrows) at 0.5 to 4.0 kg/ha for the control of foliar-feeding and soil insects. The present invention is directed to the soil application.

In certain soils, repeated applications of carbofuran have produced successive decreases in insecticidal activity. With a sufficient number and frequency of applications, the insecticide can become totally ineffective. It is therefore an object of this invention to restore the insecticidal activity of carbofuran in soils where repeated application has either substantially lessened its activity or destroyed its activity altogether.

SUMMARY OF THE INVENTION

It has now been discovered that the insecticidal activity of carbofuran in soil which has been previously treated with carbofuran and to which second or subsequent applications have produced a declining level of insecticidal activity (hereinafter referred to as "problem soil") can be restored at least in part by applying to the soil, together with an insecticidally effective amount of the insecticide, an organophosphorus compound of the formula

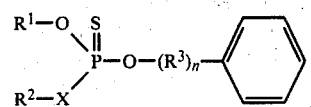

in which
$R^1$ is $C_1$-$C_4$ alkyl,
$R^2$ is $C_1$-$C_4$ alkyl,
$R^3$ is $C_1$-$C_4$ alkylene,
X is oxygen or sulfur, and
n is zero or one, in an amount sufficient to restore at least a portion of the lost activity. This is particularly surprising in view of the fact that organophosphorus compounds within the above formula have little or no insecticidal activity of their own.

Within the scope of the above formula, certain compounds are preferred, namely those having the formula

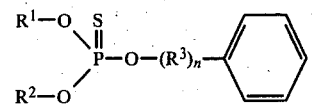

in which $R^1$, $R^2$, $R^3$, and n are as defined above.

The term "alkyl" is used in its normal sense and is intended to include both straight-chain and branched-chain groups. Examples are methyl, ethyl, propyl, isopropyl, butyl, t-butyl, etc. The term "alkylene" designates multiples of the methylene radical —$CH_2$—, optionally substituted with alkyl groups forming side chains. Examples include —$CH_2$— (methylene), —$CH_2CH_2$— (ethylene), —$CH_2CH_2CH_2$— (propylene), —$CH_2CH_2CH_2CH_2$— (butylene), —$CH(CH_3)CH_2CH_2$— (1-methylpropylene), —$CH(CH_2CH_3)CH_2$— (1-ethylethylene), etc. All carbon atom ranges are intended to be inclusive of their upper and lower limits.

The terms "insecticidally effective amount" and "insecticidal" refer to any amount of the compound or composition described which, when applied to the soil, will kill, interrupt the life cycle of, or delay the maturation of at least a measurable portion of the insect population residing therein.

The present invention resides in an insecticidal composition for use in problem soil comprising an insecticidally effective amount of carbofuran and an amount of an organophosphorus compound within the above description sufficient to restore at least a portion of the carbofuran activity; a method of controlling insects in problem soil comprising applying such a composition to the soil; and a method of restoring the insecticidal activity of carbofuran in problem soil comprising applying an effective amount of the organophosphorus compound to the soil in conjunction with the carbofuran.

DETAILED DESCRIPTION OF THE INVENTION

Carbofuran is a commercially available material. It is manufactured by the simultaneous thermal rearrangement and cyclization of 1-methallyloxy-2-nitrobenzene to form 2,3-dihydro-2,2-dimethyl-7-nitrobenzofuran, which is then reduced to the amine, then diazotized and converted to 2,3-dihydro-2,2-dimethylbenzofuran-7-ol, and then esterified with methyl isocyanate. In an alternative procedure, 2-methallyloxyphenol is thermally rearranged and cyclized to form 2,3-dihydro-2,2-dimethylbenzofuran-7-ol, which is then treated simultaneously with methyl isocyanate and triethylamine. The starting material 2-methallyloxyphenol can be prepared by reacting catechol with potassium carbonate and potassium iodide in dry acetone under a nitrogen atmosphere. Further particulars of each of these procedures will be readily apparent to those skilled in the art.

The organophosphorus compounds described above are prepared by reacting an appropriately substituted O,O-dialkyl phosphorohalothioate (chlorine is the preferred halogen) with either a phenol or a phenyl alkanol, depending on the desired product. The reaction can be conducted in tetrahydrofuran in the presence of sodium hydride or powdered sodium hydroxide. Again, the system parameters for the process will be apparent to those skilled in the art. The starting materials are commercially available or readily prepared by known techniques.

The objects of the present invention are achieved by applying the organophosphorus additive to the soil at an agricultural field site in conjunction with carbofuran. The two compounds can be applied simultaneously in a single pre-mixed formulation, simultaneously in separate formulations, or in succession in either order. In successive application, it is preferable to add the compounds as close in time as possible.

The restorative effect of the organophosphorus additive on the carbofuran activity occurs over a wide range of ratios of the two compounds, with no critical range being apparent. It is most convenient, however, to apply the compounds at a ratio of from about 0.1:1 to about 50:1 (carbofuran:additive), preferably from about 0.5:1 to about 30:1, on a weight basis.

The following examples are offered to illustrate the restorative capabilities of the organophosphorus compounds and the utility of the composition as a whole in controlling the proliferation of insects in soil. These examples are not intended to limit or define the invention in any manner.

EXAMPLE 1

This example demonstrates the declining activity of carbofuran after repeated applications to the same soil batch, and the effectiveness of O,O-diethyl-O-phenyl phosphorothioate in restoring the activity of the carbofuran.

A sandy loam soil with a moisture content of approximately 15% by weight was mixed in a small cement mixer with sufficient technical carbofuran to provide a carbofuran content of 2.0 parts per million by weight (ppm). Separately, an aqueous suspension of eggs of the western spotted cucumber beetle (*Diabrotica undecimpunctata undecimpunctata* Mann.) was prepared, containing approximately 250 eggs per cc, held in suspension by 0.2% (by weight, relative to the water) of the commercial suspending agent Dacagin® (Diamond Alkali Company, Cleveland, Ohio).

A ten-gram soil sample was then infested with 0.2 cc of the suspension (containing approximately 50 eggs), and the remainder of the soil was placed in constant temperature storage at 85° F. (29° C.) while water was added as needed to maintain the moisture level (determined by periodic weighings). Several days later the infested soil sample was observed for the emergence of larvae (none was detected). Further soil samples were similarly infested and observed after multiples of one week of storage. The four week sample was the first to show larval emergence, indicating that the insecticidal effectiveness of the carbofuran lasted over three weeks.

The soil remaining in storage was then re-treated with carbofuran at 2.0 ppm, and a series of samples were infested one week apart as before. This time the second-week sample showed the emergence of larvae. The remaining soil was then given a third treatment at 2.0 ppm and the initial sample showed the emergence of larvae. This soil was labeled "problem soil."

To test the restorative capabilities of the organophosphorus compound, several ten-gram samples of problem soil were placed in one-ounce plastic containers and treated with 2.5 ppm of O,O-diethyl-O-phenyl phosphorothioate (in acetone solution) plus varying amounts of carbofuran ranging from 10.0 ppm down to 0.1 ppm. A second series was similarly treated using 5.0 ppm of O,O-diethyl-O-phenyl phosphorothioate, and a third series was treated using 10.0 ppm. Additional series were treated with carbofuran alone and O,O-diethyl-O-phenyl phosphorothioate alone (at varying dosages). A final series consisted of carbofuran treatments on non-problem soil (i.e., soil never before treated with carbofuran). All samples were thoroughly mixed, then infested with approximately fifty Diabrotica eggs as described above. A piece of Romaine lettuce leaf was placed in each container. Seven to ten days later, the leaves were examined for evidence of larval feeding.

In samples where the carbofuran had destroyed the insect population, the leaves were intact. In samples where the carbofuran was ineffective, much of the leaf tissue had been eaten away. The break-point dosage in each series, i.e., the point above which the insecticidal activity was evident and below which it was not, was designated the LD-50 (lethal dose with 50% kill), and is listed in Table I. It is clear from the table that a substantial restoration of carbofuran insecticidal activity took place at each of the three application rates of organophosphorus compound, and that the 5.0 and 10.0 ppm applications completely restored the carbofuran activity. It is also evident that the organophosphorus compound itself has no insecticidal activity (the designation ">10" signifies that no insecticidal activity was observed at a dosage of 10 ppm).

TABLE I

RESTORATION OF CARBOFURAN ACTIVITY IN PROBLEM SOIL

Additive:

| Test Chemicals | LD-50 Values on Diabrotica Larvae (ppm) |
|---|---|
| Non-problem soil: | |
| Carbofuran alone | 0.2 |
| Problem soil: | |
| Carbofuran alone | 2.0 |
| Carbofuran plus additive (at 2.5 ppm) | 0.5[(a)] |
| Carbofuran plus additive (at 5.0 ppm) | 0.2[(a)] |
| Carbofuran plus additive (at 10.0 ppm) | 0.2[(a)] |

TABLE I-continued
RESTORATION OF CARBOFURAN ACTIVITY
IN PROBLEM SOIL

Additive:

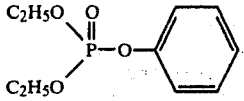

| Test Chemicals | LD-50 Values on Diabrotica Larvae (ppm) |
|---|---|
| Additive alone | >10.0[b] |

Notes:
[a]Measured in terms of carbofuran.
[b]Measured in terms of additive.

EXAMPLE 2

This example demonstrates the restorative capabilities of three organophosphorus compounds, each applied in a 1:1 weight ratio with carbofuran. The three compounds were as follows:

O,O-Diethyl-O-phenyl phosphorothioate

O,O-Diethyl-O-benzyl phosphorothioate

O-Ethyl-S-ethyl-O-phenyl phosphorodithioate

The test procedure was the same as that described in Example 1 above, except that the weight ratio of carbofuran to the organophosphorus additive was held constant at 1:1, and two replications of each test were run.

The results are shown in Table II, where it is clear that each additive served to restore a substantial amount of the insecticidal activity of carbofuran. While the use of a constant weight ratio precluded the determination of the amount required to completely restore the carbofuran activity, the benefit obtained from the inclusion of each additive is clear. Two of the three additives showed no insecticidal activity of their own, while the third showed very little. Differences between the activities reported in this table and those reported in Table I reflect the fact that different potting soils were used and the tests were run at different times of the year. Again, the ">" signs indicate that no insecticidal activity was observed at the dosages indicated.

TABLE II
RESTORATION OF CARBOFURAN ACTIVITY
IN PROBLEM SOIL

Additive:

A 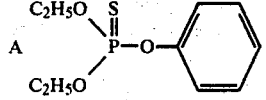

B 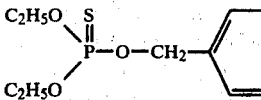

C 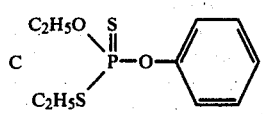

| Test Chemicals | LD-50 Values on Diabrotica Larvae (ppm) (Average of Two Replications) |
|---|---|
| Non-problem soil: | |
| Carbofuran alone | 0.75 |
| Problem soil: | |
| Carbofuran alone | >20.0 |
| Carbofuran plus Additive A (1:1) | 7.5[a] |
| Carbofuran plus Additive B (1:1) | 7.5[a] |
| Carbofuran plus Additive C (1:1) | 5.0[a] |
| Additive A alone | >20.0[b] |
| Additive B alone | >20.0[b] |
| Additive C alone | 15.0[b] |

Notes:
[a]Measured in terms of carbofuran.
[b]Measured in terms of additives.

METHODS OF APPLICATION

The compositions of the present invention are most useful in controlling soil insects when applied directly to the soil. Both carbofuran and the organophosphorus additive can be combined in a single formulation, or each can be applied in a separate formulation. Common agricultural formulations can be used, the most appropriate types being determined by the physical properties of the active ingredients, the environmental conditions, the types of crop to be protected, and other such factors. Such formulations typically contain additional, usually inert ingredients, such as diluents, carriers, wetting agents, dispersing agents, emulsifiers, suspending agents, etc. The most likely formulations for these compositions are wettable powders, flowable pastes, and granules.

Wettable powders are water-dispersable powders containing the active ingredient(s), an inert solid filler, and one or more surface-active agents to enhance wetting and prevent heavy flocculation when suspended in water. Typical solid fillers include natural clays, talcs, diatomaceous earth, and synthetic mineral fillers derived from silica and silicates. Typical surface-active agents include alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols.

Flowable pastes are concentrated suspensions of a solid active ingredient in an aqueous system. The solid particles are typically under 5 mm in diameter, and are kept in suspension by suspending agents. Typical suspending agents include low-viscosity methyl cellulose, water-soluble low-viscosity partially hydrolyzed polyvinyl alcohols, polyoxyethylene sorbitan esters of mixed fatty acid rosin acids, purified sodium lignin sulfonates, sodium salts of polymerized alkaryl and aryl alkyl sulfonic acids, methyl hydroxyethyl cellulose, and carboxymethyl cellulose.

Granules are particulate compositions with the active ingredients adhering to or distributed throughout an inert carrier about 1 to 2 millimeters in diameter. The carrier is generally of mineral origin, and falls within one of two types. The first are porous, absorptive preformed particles, such as attapulgite or heat expanded vermiculite, upon which a solution of the active ingredient is sprayed. The second are powdered materials to which the active ingredient is added prior to formation of the granule. Such materials include kaolin clays, hydrated attapulgite, or bentonite clays in the form of sodium, calcium, or magnesium bentonites. Water-soluble salts may also be present to help the granules disintegrate in water when such is desired. Surface-active agents are sometimes included to aid in the leaching of the active ingredient from the granule to the surrounding soil.

Soil application can be accomplished by any conventional technique, such as discing, dragging, or mixing operations, or spraying or sprinkling over the surface of the soil. The compositions can also be added to irrigation water so that they will accompany the water as it penetrates the soil. In-furrow application prior to the planting of seeds, however, is preferred.

Amounts required for insecticidal effectiveness will depend on the nature of the insects to be controlled as well as the prevailing conditions. Insect control is usually achieved at application rates ranging from about 0.01 to about 50 pounds of carbofuran per acre, preferably from about 0.1 to about 25 pounds per acre.

What is claimed is:

1. An insecticidal composition based on the insecticide 2,3-dihydro-2,2-dimethyl-7-benzofuranyl methylcarbamate for use in soil which has been previously treated with said insecticide and to which second or subsequent applications of said insecticide have produced a declining level of insecticidal activity, consisting essentially of
    (a) an insecticidally effective amount of said insecticide, and
    (b) an amount of an organophosphorus compound sufficient to restore at least a portion of the insecticidal activity of said insecticide, said organophosphorus compound having the formula

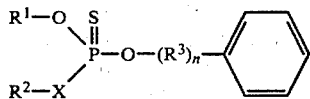

in which
$R^1$ is $C_1$-$C_4$ alkyl,
$R^2$ is $C_1$-$C_4$ alkyl,
$R^3$ is $C_1$-$C_4$ alkylene,
X is oxygen or sulfur, and
n is zero or one;
the weight ratio of insecticide to organophosphorus compound being about 1:1.

2. A composition according to claim 1 in which said organophosphorus compound has the formula

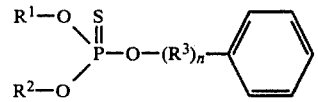

in which
$R^1$ is $C_1$-$C_4$ alkyl,
$R^2$ is $C_1$-$C_4$ alkyl,
$R^3$ is $C_1$-$C_4$ alkylene, and
n is zero or one.

3. A composition according to claim 1 in which $R^1$ is ethyl, $R^2$ is ethyl, X is oxygen, and n is zero.

4. A composition according to claim 1 in which $R^1$ is ethyl, $R^2$ is ethyl, $R^3$ is methylene, X is oxygen, and n is one.

5. A composition according to claim 1 in which $R^1$ is ethyl, $R^2$ is ethyl, X is sulfur, and n is zero.

6. A method of controlling insects residing in soil which has been previously treated with the insecticide 2,3-dihydro-2,2-dimethyl-7-benzofuranyl methylcarbamate and to which second or subsequent applications of said insecticide have produced a declining level of insecticidal activity, which comprises applying to said soil both
    (a) an insecticidally effective amount of said insecticide, and
    (b) an amount of an organophosphorus compound sufficient to restore at least a portion of the insecticidal activity of said insecticide, said organophosphorus compound having the formula

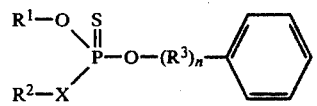

in which
$R^1$ is $C_1$-$C_4$ alkyl,
$R^2$ is $C_1$-$C_4$ alkyl,
$R^3$ is $C_1$-$C_4$ alkylene,
X is oxygen or sulfur, and
n is zero or one;
the weight ratio of insecticide to organophosphorus compound being about 1:1.

7. A method according to claim 6 in which said organophosphorus compound has the formula

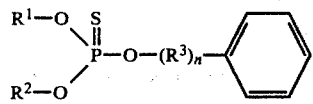

in which
$R^1$ is $C_1$-$C_4$ alkyl,
$R^2$ is $C_1$-$C_4$ alkyl,
$R^3$ is $C_1$-$C_4$ alkylene, and
n is zero or one.

8. A method according to claim 6 in which $R^1$ is ethyl, $R^2$ is ethyl, X is oxygen, and n is zero.

9. A method according to claim 6 in which $R^1$ is ethyl, $R^2$ is ethyl, $R^3$ is methylene, X is oxygen, and n is one.

10. A method according to claim 6 in which $R^1$ is ethyl, $R^2$ is ethyl, X is sulfur, and n is zero.

* * * * *

UNITED STATES PATENT AND TRADEMARK OFFICE
CERTIFICATE OF CORRECTION

PATENT NO. : 4,419,350

DATED : December 6, 1983

INVENTOR(S) : Peter E. Letchworth et al.

It is certified that error appears in the above-identified patent and that said Letters Patent is hereby corrected as shown below:

The formula appearing in Columns 4 and 5 should read as follows:

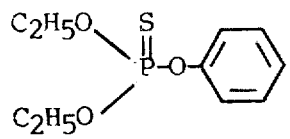

Signed and Sealed this

Twenty-fifth Day of September 1984

[SEAL]

Attest:

GERALD J. MOSSINGHOFF

Attesting Officer     Commissioner of Patents and Trademarks